United States Patent [19]

Tadanier et al.

[11] 4,427,662
[45] Jan. 24, 1984

[54] 3-AMINO-3-DEMETHOXYFORTIMICINS, PHARMACEUTICAL COMPOSITIONS THEREOF AND METHOD OF USE

[75] Inventors: John S. Tadanier, Waukegan, Ill.; Robert Hallas, Kenosha, Wis.; Leslie A. Freiberg; David J. Bacino, both of Waukegan, Ill.

[73] Assignee: Abbott Laboratories, North Chicago, Ill.

[21] Appl. No.: 366,798

[22] Filed: Apr. 9, 1982

[51] Int. Cl.$^3$ .................... A61K 31/71; C07H 15/22
[52] U.S. Cl. .................................. 424/180; 536/16.1
[58] Field of Search ................... 424/180; 536/16.1

[56] References Cited

U.S. PATENT DOCUMENTS 4,124,756 11/1978 Martin et al. ..................... 536/16.1
4,187,297 2/1980 Martin et al. ..................... 536/16.1
4,269,970 5/1981 Tadanier et al. .................. 536/16.1

*Primary Examiner*—Johnnie R. Brown
*Attorney, Agent, or Firm*—Dennis K. Shelton

[57] ABSTRACT

Disclosed herein are fortimicin derivatives represented by the formula:

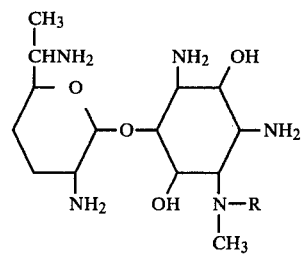

wherein R is hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, loweracyl, aminoloweracyl, diaminoloweracyl, hydroxyloweracyl, N-loweralkylaminoloweracyl, N,N-diloweralkylaminoloweracyl, or aminohydroxyloweracyl, and the pharmaceutically acceptable salts thereof. Also disclosed are intermediates useful in the preparation of these compounds and compositions of these compounds together with a pharmaceutically acceptable carrier and/or diluent.

20 Claims, No Drawings

3-AMINO-3-DEMETHOXYFORTIMICINS, PHARMACEUTICAL COMPOSITIONS THEREOF AND METHOD OF USE

BACKGROUND OF THE INVENTION

The present invention relates to 3-amino-3-demethoxyfortimicin A, 3-amino-3-demethoxyfortimicin B, 4-N-substituted derivatives of 3-amino-3-demethoxyfortimicin, B, and their pharmaceutically acceptable salts, to intermediates useful in the preparation of these compounds, and to compositions comprising these compounds and pharmaceutically acceptable carriers or diluents.

The fortimicins are a relatively new class of aminoglycoside antibiotics which are useful in the treatment of susceptible bacterial infections. Fermentation produced fortimicins include fortimicin A, disclosed in U.S. Pat. No. 3,976,768; fortimicin B, disclosed in U.S. Pat. No. 3,931,400; and fortimicin C, disclosed in U.S. Pat. Nos. 4,048,015 and 4,097,428. Other fermentation produced fortimicin factors have also been isolated.

Once an aminoglycoside antibiotic has been in clinical use for a period of time, resistant microorganisms may develop. In many cases, the resistance is R-factor mediated and is attributed to the ability of the bacteria to enzymatically modify the amino or hydroxyl groups of the aminoglycoside antibiotics and thereby reduce or eliminate their antibacterial properties. Thus, there is also a need for new entities which can be held in reserve to combat strains which have become resistant to treatment by the clinically used antibiotics. In the past, it has been found that the antibacterial and pharmacological properties of many naturally produced aminoglycoside antibiotics can be altered by structural modifications. As an example, certain chemical modifications in the gentamicin and kanamycin family of aminoglycoside antibiotics provide structures which are less toxic than the parent antibiotic. Further, in the same series, certain modifications alter the antibacterial spectrum advantageously either by increasing the intrinsic activity or increasing activity against resistant strains.

It has been previously determined that certain chemical modification of the parent fortimicins can also result in derivative compounds which exhibit increased antibacterial activity with respect to particular microorganisms, reduced toxicity, or equivalent or reduced activity, but nevertheless are useful as reserve antibiotics in the event resistant strains develop after a period of clinical use of one or more of the fortimicins. For example, 4-N-acyl and -alkyl derivatives of fortimicin B and techniques for forming these compounds are disclosed in U.S. Pat. Nos. 4,091,032; 4,155,902; 4,173,564; 4,174,312; 4,220,775 and 4,231,924; the disclosures of which are specifically incorporated herein by reference; and others. The fortimicin compounds have also been demethylated at the 3-position to provide useful derivatives. For example, 3-O-demethylfortimicins are disclosed in U.S. Pat. Nos. 4,124,756; 4,187,297; 4,220,756; 4,230,848; 4,242,503; 4,251,516 and 4,293,689.

While a number of fortimicin derivatives have been made to date, and valuable therapeutic agents have been identified, it is desirable to obtain new fortimicin antibiotics which exhibit a broader or different antibacterial spectrum, less toxicity, oral activity, or other desirable properties, or which can be held in reserve and used to treat infections caused by organisms which become resistant to other fortimicin therapy.

The present invention relates to novel 3-amino-3-demethoxyfortimicins which exhibit antibacterial activity. More specifically, the present invention relates to 3-amino-3-demethoxyfortimicin A, 3-amino-3-demethoxyfortimicin B, and 4-N-substituted-3-amino-3-demethoxyfortimicin B, to intermediates and processes useful in the production of these novel compounds, and to compositions comprising these compounds and a pharmaceutically acceptable carrier or diluent.

DETAILED DESCRIPTION OF THE INVENTION

The 3-amino-3-demethoxyfortimicin compounds of the invention differ from fortimicin A, fortimicin B, and fortimicin B derivatives, in their substitution of an amino group for the methoxy group normally present at the 3-position of the cyclitol ring of the aminoglycoside. These 3-amino-3-demethoxyfortimicins can be represented by the following structural formula:

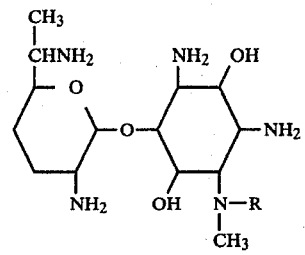

wherein R is hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N-N-diloweralkylaminohydroxyloweralkyl, loweracyl, aminoloweracyl, diaminoloweracyl, hydroxyloweralkyl, N-loweralkylaminoloweralkyl, N,N-diloweralkylaminoloweracyl, or aminohydroxyloweracyl, and the pharmaceutically acceptable salts thereof.

Intermediates of the invention useful in preparing the 3-amino-3-demethoxyfortimicins of formula I can be represented by the structural formula:

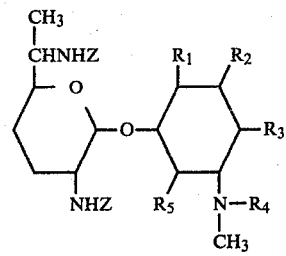

wherein $R_1$ is —NHZ; $R_2$ is hydroxyl; or $R_1$ and $R_2$ can be taken together to form a carbamate ring; $R_3$ is hydroxyl, methanesulfonyl or azido; $R_4$ is hydrogen, loweralkyl, hydroxyloweralkyl, loweracyl, hydroxyloweracyl, or a monocyclicarylmethyloxycarbonyl-protected aminoloweralkyl, diaminoloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, aminoloweralkyl, diaminoloweracyl, N-loweralkylaminoloweracyl, N,N-diloweralkylaminoloweracyl, or aminohydroxyloweracyl; $R_5$ is hydroxy; or $R_4$ and $R_5$ can be taken together to form an oxazolidine ring; or $R_1$ and $R_5$ can be taken together to form a carbamate ring; and Z is a monocyclicarylmethoxycarbonyl amine protecting group.

The term "loweralkyl", as used herein, refers to straight or branched chain alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 2-methylpentyl, n-heptyl and the like.

The term "loweracyl" as used herein refers to acyl groups represented by the formula

wherein $R_7$ is loweralkyl, as defined above. Representative loweracyl groups useful in the invention include acetyl, propionyl, butyryl, valeryl and the like.

The terms "aminoloweracyl", "diaminoloweracyl", etc., include the naturally occurring aminoacids such as glycyl, valyl, alanyl, sarcosyl, leucyl, isoleucyl, prolyl, seryl, and the like as well as other amino-substituted lower acyl groups such as 2-hydroxy-4-aminobutyryl. The aminoacids residue include in the above terms can be in the L- or D-configurations or a mixture thereof, with the exception of glycyl and β-alanyl.

The term "monocylicarylmethyloxycarbonyl" as used herein refers to protecting groups such as benzyloxycarbonyl, paramethylbenzyloxycarbonyl, paramethoxybenzyloxycarbonyl or orthonitrobenzyloxycarbonyl which are commonly used as N-protecting groups in peptide synthesis and in other areas where N-protection is required.

The term "pharmaceutically acceptable salts", as used herein, refers to the nontoxic acid addition salts of the compounds of this invention. These salts can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salts of this invention can be per-N-salts.

The 3-amino-3-demethoxyfortimicin compounds of the invention may be prepared from tri-N-protected-3-O-demethyl fortimicin B according to the following reaction scheme:

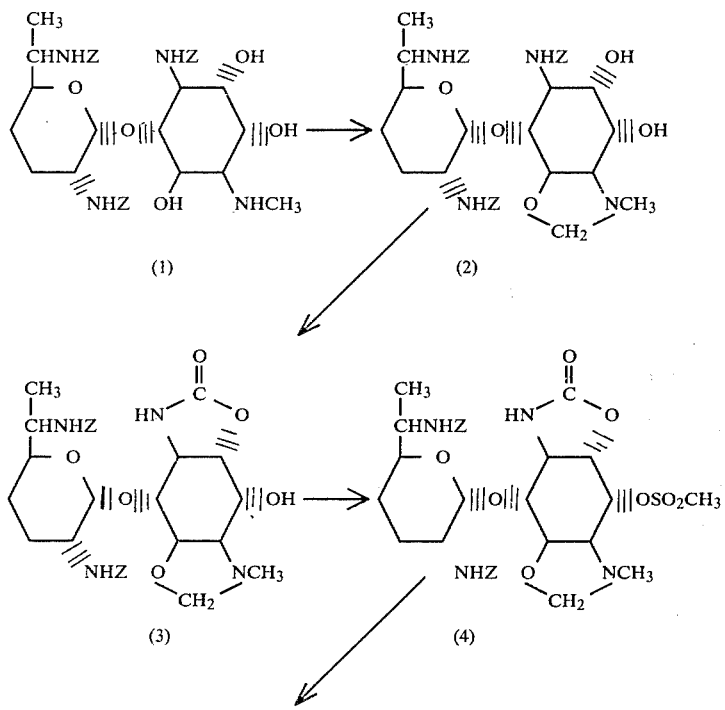

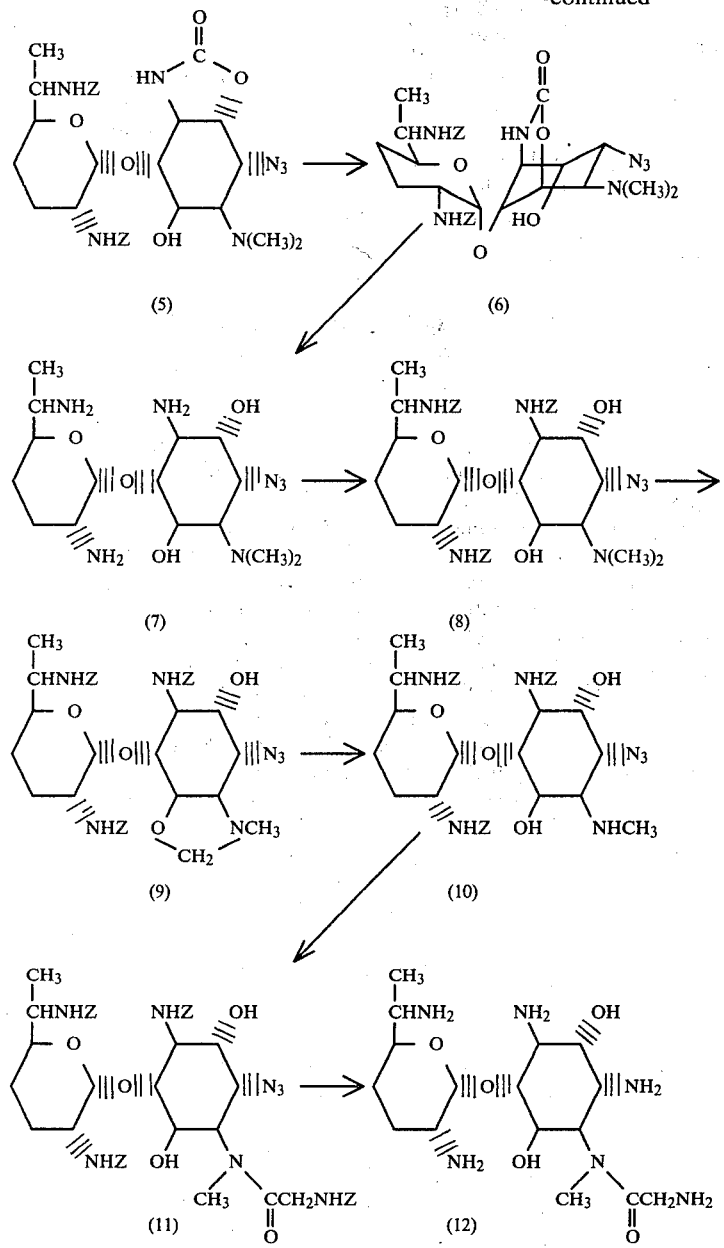

In the foregoing reaction scheme, N-protected-3-O-demethylfortimicin B (1), such as 1,2',6'-tri-N-benzyloxycarbonyl-3-O-demethylfortimicin B is used as the starting material. The 1,2',6'-tri-N-benzyloxycarbonyl-3-O-demethylfortimicin B may be obtained from the reaction of 3-O-demethylfortimicin B with N(benzyloxycarbonyloxy)-succinimide as disclosed in U.S. Pat. Nos. 4,124,756 and 4,187,297, or from the selective hydrolysis of 1,2',6',2''-tetra-N-benzyloxycarbonyl-3-O-demethylfortimicin A.

Treatment of N-protected-3-O-demethylfortimicin B (1) with formalin in methanol yields the 4,5-formaldehyde oxazolidine (2), which is converted to the corresponding 1,2-carbamate (3) upon treatment with sodium hydride in N,N-dimethylformamide. The 1,2-carbamate-4,5-formaldehyde oxazoline (3) is treated with methanesulfonyl chloride in pyridine to produce the corresponding 3-methanesulfonate (4). Treatment of the 3-methanesulfonate (4) with sodium cyanoborohydride and sodium azide in methanol in the presence of acetic acid and formalin yields the 3-azido-4-N-methyl-1,2-carbamate (5), which rearrange in aqueous methanol to produce the corresponding 3-azido-4-N-methyl-1,5-carbamate (6). Basic hydrolysis of the 1,5-carbamate (6) results in the 3-azido-4-N-methyl-3-demethoxyfortimicin B (7), which is converted to the 1,2',6'-tri-N-protected derivative (8), such as by treatment with N-(benzyloxycarbonyloxy)-succinimide. Upon treatment with iodine and sodium acetate in methanol under irradiation, and subsequent treatment with formalin, the tri-N-protected derivative (8) is converted to the corresponding 3-azido-4,5-formaldehyde oxazolidine (9), which yields the tri-N-protected-3-azido-3-demethoxyfortimicin B (10) upon mild acid-catalyzed hydrolysis in the presence of hydroxylamine hydrochloride as an aldehyde scavenger.

The tri-N-protected-3-azido-3-demethoxyfortimicin B compound (10) may be converted to 3-amino-3-demethoxyfortimicin A (12) by acylation with N-(N-benzyloxycarbonylglycyloxy-succinimide to form 1,2',6',2"-tetra-N-protected-3-azido-3-demethoxyfortimicin A (11) and subsequent catalytic hydrogenation. Alternatively, the tri-N-protected-3-azido-3-demethoxyfortimicin B (10) can be directly catalytically hydrogenated to yield 3-amino-3-demethoxyfortimicin B. The tri-N-protected-fortimicin B intermediates can also be alkylated and acylated at the 4-N-position to produce 4-N-alkyl- or 4-N-acyl-substituted-3-amino-3-O-demethoxyfortimicin B by 4-N-alkylation and 4-N-acylation techniques well known in the art, such as by techniques referred to in the issued patents cited supra.

The foregoing reaction scheme may be better understood in connection with the following examples:

EXAMPLE 1

1,2',6'-Tri-N-benzyloxycarbonyl-3-O-demethylfortimicin B 4,5-formaldehyde oxazolidine A solution prepared from 4.02 g. of 1,2',6'-tri-N-benzyloxycarbonyl-3-O-demethylfortimicin B (1), 2 ml. of 37% formalin, and 400 ml. of methanol is stirred at room temperature for 18 hours. The solvent is evaporated under reduced pressure leaving 4.08 g. of 1,2',6'-tri-N-benzyloxycarbonyl-3-O-demethylfortimicin B 4,5-formaldehyde oxazolidine, as a white glass: $\delta(CDCl_3)$ 1.02 d ($J_{6',7'}=6.4$ Hz, 6'-CH$_3$) 2.15 (NCH$_3$).

EXAMPLE 2

3-O-demethyl-2',6'-di-N-benzyloxycarbonylfortimicin B 1,2-carbamate 4,5-formaldehyde oxazolidine A magnetically stirred solution of 6.01 g. of 1,2',6'-tri-N-benzyloxycarbonyl-3-O-demethylfortimicin B 4,5-formaldehyde oxazolidine in 120 ml. of N,N-dimethylformamide is cooled in an ice bath and purged with nitrogen. Sodium hydride (1.84 g. of a 57% oily dispersion) is added and stirring is continued with cooling for 1 hour and then at room temperature for an additional 18 hours. The resulting solution is cooled in an ice bath and 20 ml. of a solution of 1:2 acetic acid-water is added cautiously. The resulting solution is shaken with a mixture of 600 ml. of 5% aqueous sodium bicarbonate and 300 ml. of CHCl$_3$. The CHCl$_3$ solution is separated and extracted four times with 240-ml. portions of CHCl$_3$. The CHCl$_3$ solutions are combined and dried over MgSO$_4$. The CHCl$_3$ is evaporated under reduced pressure and the residual N,N-dimethylformamide is removed by co-distillation with toluene under reduced pressure, leaving 6.13 g. of brown foam. The latter is chromatographed on a column of 450 g. of silica gel prepared and eluted with ethyl acetate-triethylamine (20:01) to yield 3.21 g. of 3-O-demethyl-2',6'-di-N-benzyloxycarbonylfortimicin B 1,2-carbamate 4,5-formaldehyde oxazolidine as a white glass: $\delta(CDCl_3)$: 1.14 d (6.8 Hz, 6'-CH$_3$); 2.25 (NCH$_3$); 3.78 d, 4.59 d (J=2 Hz, O-CH$_2$-NCH$_3$); $\bar{\nu}$max (CDCl$_3$) 3602, 3440, 3320s, 1770, 1718 cm$^{-1}$

EXAMPLE 3

3-O-Methanesulfonyl-3-O-demethyl-2',6'-di-N-benzyloxycarbonylfortimicin B 1,2-carbamate 4,5-formaldehyde oxazolidine To a magnetically stirred solution of 1.01 g. of 3-O-demethyl-2',6'-di-N-benzyloxycarbonylfortimicin B 1,2-carbamate 4,5-formaldehyde oxazolidine in 18 ml. of pyridine, cooled in an ice bath, is added 0.36 ml. of methanesulfonyl chloride. Stirring is continued with cooling for 1 hour and then at room temperature overnight. The resulting solution is shaken with a mixture of chloroform and 5% aqueous sodium bicarbonate. The chloroform solution is separated and dried over MgSO$_4$. Evaporation of the chloroform leaves 1.20 g. of 3-O-methanesulfonyl-3-O-demethyl-2',6'-di-N-benzyloxycarbonylfortimicin B 1,2-carbamate 4,5-formaldehyde oxazolidine as a glass: $\delta(CDCl_3)$ 1.26 d ($J_{6',7'}=6.7$ Hz, 6'-CH$_3$), 2.39 (NCH$_3$), 3.10 (OSO$_2$CH$_3$), 3.89 d, 4.62 d (J=2.6 Hz, OCH$_2$-NCH$_3$). $\nu$max (CDCl$_3$) 3443, 3298, 1778, 1715, 1178 cm$^{-1}$.

EXAMPLE 4

3-Demethoxy-3-azido-4-N-methyl-2',6'-di-N-benzyloxycarbonylfortimicin B 1,2-carbamate and 3-demethoxy-3-azido-4-N-methyl-2',6'-di-N-benzyloxycarbonylfortimicin B 1,5-carbamate A suspension prepared from 1.032 g. of 3-O-methanesulfonyl-3-O-demethyl-2',6'-di-N-benzyloxycarbonylfortimicin B 1,2-carbamate 4,5-formaldehyde oxazolidine, 0.2357 g. of sodium cyanoborohydride, 0.8 g. sodium azide, 0.8 ml. of 37% formalin, 0.4 ml. of acetic acid and 10 ml. of methanol is stirred at room temperature for 40 hours and then shaken with a mixture of chloroform and 5% aqueous sodium bicarbonate. The chloroform solution is separated and dried over MgSO$_4$. Evaporation of the chloroform under reduced pressure leaves 0.8946 g. of crude 3-demethoxy-3-azido-4-N-methyl-2',6'-di-N-benzyloxycarbonylfortimicin B 1,2-carbamate: $\delta(CDCl_3)$ 1.15 d ($J_{6',7'}=6$ Hz, 6'-CH$_3$), 2.38 [N(CH$_3$)$_2$]; $\bar{\nu}$max (CHCl$_3$) 3442, 3318, 2106, 1774, 1712 cm$^{-1}$.

A milky suspension prepared from 0.8321 g. of crude 3-demethoxy-3-azido-4-N-methyl-2',6'-di-N-benzyloxycarbonylfortimicin B 1,2-carbamate, 80 ml. of methanol and 25 ml. of 5% aqueous sodium bicarbonate is stirred at room temperature for 24 hours and then shaken with a mixture of chloroform and 5% aqueous sodium bicarbonate. The chloroform solution is separated and dried over MgSO$_4$. Evaporation of the chloroform under reduced pressure leaves 0.8244 g. of 3-demethoxy-3-azido-4-N-methyl-2',6'-di-N-benzyloxycarbonylfortimicin B 1,5-carbamate.

A sample (9.80 g.) of the product prepared as described above is chromatographed on a column of 400 g. of silica gel packed and eluted with ethyl acetate to give 5.61 g. of pure 3-demethoxy-3-azido-4-N-methyl-2',6'-di-N-benzyloxycarbonylfortimicin B 1,5-carbamate: $[\alpha]_D^{28}+93°$ (C 1.0, CH$_3$OH), $\delta(CDCl_3)$ 1.15 d; $\bar{\nu}$ ($J_{6',7'}=6.5$ Hz, 6'-CH$_3$), 2.39 [N(CH$_3$)$_2$] max (CHCl$_3$) 3520, 3442, 2112, 1718 cm$^{-1}$.

Analysis Calcd. for C$_{32}$H$_{41}$N$_7$O$_9$: C, 57.56; H, 6.19; N, 14.68. Found: C, 56.94; H, 6.03; N, 14.57.

EXAMPLE 5

3-Azido-3-demethoxy-4-N-methylfortimicin B

A solution prepared from 5.61 g. of 3-demethoxy-3-azido-4-N-methyl-2',6'-di-N-benzyloxycarbonylfortimicin B 1,5-carbamate, 70 ml. of 6 N-potassium hydroxide and 140 ml. of ethanol is heated at 85°–90° overnight. 100 ml. of water is added and the resulting solution is brought to pH 1 by addition of 1 N hydrochloric acid. The solvent is evaporated under reduced pressure, and the residue is triturated with methanol. Insoluble salts are removed by filtration. Evaporation of the methanol from the filtrate leaves 5.67 g. of crude 3-azido-3-demethoxy-4-N-methylfortimicin B, which is chromatographed on a column of 350 g. of silica gel packed and eluted with a solvent system composed of chloroform-methanol-ammonium hydroxide (1:1:0.1) to yield 2.73 g. of pure 3-azido-3-demethoxy-4-N-methylfortimicin B.

3-Azido-3-demethoxy-4-N-methylfortimicin B (2.73 g.) is dissolved in 200 ml. of methanol and the resulting solution is brought to pH 1 by addition of 0.4 N-hydrochloric acid in methanol. The solvent is evaporated under reduced pressure and residual hydrochloric acid is removed by co-distillation under reduced pressure first with ethanol and then with methanol to give 3.10 g. of 3-azido-3-demethoxy-4-N-methylfortimicin B tetrahydrochloride: $\delta(D_2O, PD\ 4.86)$ 1.36 d ($J_{6',7'}=6.8$ Hz, 6'-CH$_3$), 3.09 [N(CH$_3$)$_2$], 5.37 d ($J_{1',2'}=3.2$ Hz, 1'-H); m/z: M$^{+\circ}$, Meas. 374.2528, Calcd. for C$_{15}$H$_{32}$N$_7$O$_4$ 374.2516; Cyclitol Meas. 234.1413; Calcd. for C$_8$H$_{18}$N$_5$O$_3$, 232.1410 Diaminosugar, Meas. 143.1184, Calcd. for C$_7$H$_{15}$N$_2$O, 143.1184.

EXAMPLE 6

1,2',6'-Tri-N-benzyloxycarbonyl-3-azido-3-demethoxy-4-N-methylfortimicin B

A suspension of 3.07 g. of the tetrahydrochloride of 3-azido-3-demethoxy-4-N-methylfortimicin B, 4.85 g. of N-(benzyloxycarbonyloxy)-succinimide, 3.63 ml. of triethylamine, 24 ml. of water and 96 ml. of methanol is stirred in an ice bath for 3 hours and then at room temperature overnight. The resulting solution is shaken with a mixture of chloroform and 5% aqueous sodium bicarbonate. The chloroform solution is separated and dried over MgSO$_4$. Evaporation of the solvent under reduced pressure leaves 4.83 g. of crude 1,2',6'-tri-N-benzyloxycarbonyl-3-azido-3-demethoxy-4-N-methylfortimicin B, which is chromatographed on a column of 400 g. of silica gel packed and eluted with a solvent system composed of ethyl acetate-hexane-triethylamine (4:1:0.1) to yield 4.05 of pure 1,2',6'-tri-N-benzyloxycarbonyl-3-azido-3-demethoxy-4-N-methylfortimicin B: $\delta$(CDCl$_3$) 1.02 d ($J_{6',7'}=6.0$ Hz, 6'-CH$_3$), 2.41 [N(CH$_3$)$_2$]; $\bar{\nu}$max (CHCl$_3$) 3441, 3341, 2106, 1711 cm$^{-1}$.

EXAMPLE 7

1,2',6'-Tri-N-benzyloxycarbonyl-3-azido-3-demethoxyfortimicin B 4,5-formaldehyde oxazolidine and 1,2',6'-Tri-N-benzyloxycarbonyl-3-azido-3-demethoxyfortimicin B A stirred solution of 3.71 g. of 1,2',6'-tri-N-benzyloxycarbonyl-3-azido-3-demethoxy-4-N-methylfortimicin B, 1.86 g. of iodine, 6.53 g. of sodium acetate trihydrate and 160 ml. of methanol is irradiated for 4 hours with a 150 Watt flood lamp. Sodium thiosulfate (2.95 g.) is added and stirring is continued until the solution becomes colorless. Formalin (0.7 ml., 37%) is added and the resulting solution is shaken with a mixture of chloroform and 5% aqueous sodium bicarbonate. The chloroform solution is separated and dried over MgSO$_4$. Evaporation of the chloroform under reduced pressure leaves 3.64 g. of 1,2',6'-tri-N-benzyloxycarbonyl-3-azido-3-demethoxyfortimicin B 4,5-formaldehyde oxazolidine as a white glass: $\delta$(CDCl$_3$) 0.99 d ($J_{6',7'}=6.5$ Hz, 6'-CH$_3$); 2.29 (NCH$_3$); 3.84 d, 4.58 d (J=2.5 Hz, OCH$_2$NCH$_3$); $\bar{\nu}$max (CHCl$_3$) 3570, 3440, 3340, 2108, 1712 cm$^{-1}$.

A solution of 3.60 g. of 1,2',6'-tri-N-benzyloxycarbonyl-3-azido-3-demethoxyfortimicin B 4,5-formaldehyde oxazolidine, 1.84 g. of hydroxylamine hydrochloride, 3.8 ml. of acetic acid and 130 ml. of methanol is heated under reflux for 1 hour. The resulting solution is cooled to room temperature and shaken with a mixture of chloroform and 5% aqueous sodium bicarbonate. The chloroform solution is separated and dried over MgSO$_4$. Evaporation of the chloroform under reduced pressure leaves 3.46 g. of 1,2',6'-tri-N-benzyloxycarbonyl-3-azido-3-demethoxyfortimicin B: $\delta$(CDCl$_3$) 0.99 d ($J_{6',7'}=6.3$ Hz, 6'-CH$_3$), 2.38 (NCH$_3$); $\bar{\nu}$max (CHCl$_3$) 3440, 3350, 2110, 1712 cm$^{-1}$.

EXAMPLE 8

1,2',6',2''-Tetra-N-benzyloxycarbonyl-3-azido-3-demethoxyfortimicin A

A magnetically stirred solution of 3.42 g. of 1,2',6'-tri-N-benzyloxycarbonyl-3-azido-3-demethoxyfortimycin B, 2.68 g. of N-benzyloxycarbonylglycine anhydride and 100 ml. of tetrahydrofuran is kept overnight at room temperature. The resulting solution is shaken with a mixture of chloroform and 5% aqueous sodium bicarbonate. The chloroform solution is dried over MgSO$_4$ and the chloroform is evaporated under reduced pressure to yield 4.92 g. of crude 1,2',6',2''-tetra-N-benzyloxycarbonyl-3-azido-3-demethoxyfortimicin A. Chromatography of 2.50 g. of the latter on a column of 250 g. of silica gel packed and eluted with a solvent system composed of ethyl acetate-hexane 4:1 gives 1.8 g. of pure 1,2',6',2''-tetra-N-benzyloxycarbonyl-3-azido-3-demethoxyfortimicin A: $\delta$(CDCl$_3$) 1.18 d ($J_{6',7'}=6.2$ Hz, 6'-CH$_3$); 2.91 (major); 3.06 (minor) (NCH$_3$, rotometers); $\nu$max (CHCl$_3$) 3438, 3338s, 2110, 1716, 1646 cm$^{-1}$.

EXAMPLE 9

3-Amino-3-demethoxyfortimicin A pentahydrochloride 1,2',6',2''-Tetrabenzyloxycarbonyl-3-azido-3-demethoxyfortimicin A (0.876 g.) is catalytically hydrogenated under three atmospheres of hydrogen for 3 hours in 92 ml. of 0.2 N hydrochloric acid in the presence of 0.9 g. of 5% palladium on carbon to give 551 mg. of the pentahydrochloride of 3-amino-3-demethoxyfortimicin A. The latter is converted to the salt (C$_{16}$H$_{34}$N$_6$O$_5$.5/2H$_2$SO$_2$) with AG1-X2 (SO$_4$) resin: $\delta$(D$_2$O) 1.06 d ($J_{6',7'}=7.0$ Hz), 3.19 (NCH$_3$), 5.03 d ($J_{1',2'}=3.5$ Hz, H',) m/z: M$^{+\circ}$, Meas. 390.2609; Calcd. for C$_{16}$H$_{34}$N$_6$O$_5$, 390.2591; Cyclitol, Meas. 249.1560; Calcd. for C$_9$H$_{21}$N$_4$O$_4$, 249.1563; Diaminosugar, Meas. 143.1176, Calcd. for C$_7$H$_{15}$N$_2$O, 143.1184.

EXAMPLE 10

Activity

The in vitro activity of the sulfate salt of 3-amino-3-demethoxyfortimicin A, prepared in accordance with Example 9, is determined by a two-fold dilution test using 10 ml. of Mueller-Hinton agar per Petri plate. The agar plates are innoculated with approximately 1×10$^5$ of the test organisms indicated in Table 1, delivered to the agar surface by a Steers replicator. The innoculated plates are incubated for 24 hours at 35° C. in the presence of varying concentrations of the sulfate salts 3-amino-3-demethoxyfortimicin A of Example 9, or of fortimicin A as a comparative antibiotic. The minimum inhibitory concentrations (MIC) of the antibiotics are shown in Table 1, expressed as $\mu$g./ml.

TABLE 1

| | In Vitro Activity | |
|---|---|---|
| Test Organism | Fortimicin A Sulfate | 3-Amino-3-demethoxy-fortimicin A .5/2 $H_2SO_4$ |
| Staph. aureus Smith | 1.56 | 0.78 |
| Strep. faecalis | 25 | 100 |
| Enterobacter aerogenes | 3.1 | 3.1 |
| E. coli JUHL | 3.1 | 3.1 |
| E. coli BL 3676 (Res) | 25 | 25 |
| E. coli 76-2 | 3.1 | 3.1 |
| Kleb. pneumoniae 10031 | 1.56 | 1.56 |
| Kleb. pneumoniae KY 4262 | 3.1 | 6.2 |
| Providencia 1577 | 1.56 | 3.1 |
| Pseudo. aeruginosa BMH #10 | 0.78 | 0.78 |
| Pseudo. aeruginosa KY 8512 | 6.2 | 3.1 |
| Pseudo. aeruginosa KY 8516 | 6.2 | 3.1 |
| Pseudo. aeruginosa 209 | 100 | 100 |
| Pseudo. aeruginosa 27853 | 6.2 | 3.1 |
| Sal. typhimurium Ed. #9 | 3.1 | 3.1 |
| Serratia marcescens 4003 | 1.56 | 3.1 |
| Shigella sonnei 9290 | 6.2 | 6.2 |
| Proteus rettgeri U6333 | 6.2 | 6.2 |
| Proteus vulgaris JJ | 3.1 | 3.1 |
| Proteus mirabilis Fin. #9 | 6.2 | 3.1 |

As is apparent from the foregoing, the compounds of formula I exhibit antibiotic activity against susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rettgeri, Proteus vulgaris* and *Proteus mirabilis.*

The compound of the invention may be used alone or in combination with a pharmaceutically acceptable carrier or diluent.

The compounds may be employed systemically by parenteral injection, e.g., by intramuscular, intravenous, intraperitoneal or subcutaneous routes of administration. The compounds can additionally be administered orally in those instances where it is desirable to sterilize the intestinal tract, and they can be administered topically and rectally. The compounds can also be incorporated into scrub solutions for reducing bacterial growth on such surfaces as laboratory bench tops, operating room surfaces and the like.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Resides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to inhibit growth of a susceptible organism for a particular composition and method of administration. The selected dosage level therefore depends upon the desired therapeutic effect, on the route of administration, on the duration of treatment and other factors. Generally, dosage levels of about 5 to about 200, more preferably about 10 to about 100 and most preferably about 15 to about 50 mg. of active ingredient per kg. of body weight are administered daily to a mammalian patient suffering from an infection caused by a susceptible organism. If desired, the daily dose may be divided into multiple doses for administration, e.g., two to four times per day.

What is claimed is:

1. A 3-amino-3-demethoxyfortimicin compound of the formula:

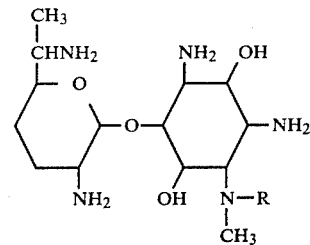

wherein R is hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, loweracyl, aminoloweracyl, diaminoloweracyl, hydroxyloweracyl, N-loweralkylaminoloweracyl, N,N-diloweralkylaminoloweracyl, or aminohydroxyloweracyl, and the pharmaceutically acceptable salts thereof.

2. The compound of claim 1 wherein R is glycyl.

3. The compound of claim 1 wherein R is hydrogen.

4. 3-Amino-3-demethoxyfortimicin A or a pharmaceutically acceptable salt thereof.

5. 3-Amino-3-demethoxyfortimicin B or a pharmaceutically acceptable salt thereof.

6. A pharmaceutical composition comprising an antibacterially effective amount of a compound of claim 1 and a pharmaceutically acceptable carrier or diluent.

7. A pharmaceutical composition comprising an antibacterially effective amount of 3-amino-3-demethoxyfortimicin A or a pharmaceutically acceptable salt thereof and a pharmaceuticaly acceptable carrier or diluent.

8. A method of treating a mammalian patient, comprising administering an antibacterially effective amount of a compound of claim 1 to said patient.

9. A method of treating a mammalian patient, comprising administering an antibacterially effective amount of 3-amino-3-demethoxyfortimicin A or a pharmaceutically acceptable salt thereof to said patient.

10. A compound of the formula

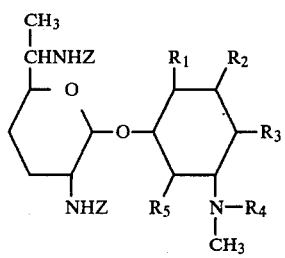

wherein $R_1$ is —NHZ; $R_2$ is hydroxyl; or $R_1$ and $R_2$ can be taken together to form a carbamate ring; $R_3$ is methanesulfonyl or azido; $R_4$ is hydrogen, loweralkyl, hydroxyloweralkyl, loweracyl, hydroxyloweracyl, or a monocyclicarylmethyloxycarbonyl-protected amino-loweralkyl, diaminoloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, aminoloweralkyl, diaminoloweracyl, N-loweralkylaminoloweracyl, N,N-diloweralkylaminoloweracyl, or aminohydroxyloweracyl; $R_5$ is hydroxy; or $R_4$ and $R_5$ can be taken together to form an oxazolidine ring; or $R_1$ and $R_5$ can be taken together to form a carbamate ring; and Z is a monocyclicarylmethyloxycarbonyl amine protecting group.

11. A compound of claim 10 wherein Z is benzyloxycarbonyl.

12. A compound of claim 11 wherein $R_1$ and $R_2$ are taken together to form a carbamate ring, and $R_4$ and $R_5$ are taken together to form an oxazolidine ring.

13. A compound of claim 12: 3-O-demethyl-2′,6′-di-N-benzyloxycarbonylfortimicin B 1,2-carbamate 4,5-oxazolidine.

14. A compound of claim 12: 3-O-methane-sulfonyl-3-O-demethyl-2′,6′-di-N-benzyloxycarbonylfortimicin B 1,2-carbamate 4,5-oxazolidine.

15. The compound of claim 11 wherein $R_1$ and $R_2$ are taken together to form a carbamate ring, $R_3$ is azido, $R_4$ is methyl and $R_5$ is hydroxyl.

16. The compound of claim 11 wherein $R_1$ and $R_5$ are taken together to form a carbamate ring, $R_2$ is hydroxyl, $R_3$ is azido and $R_4$ is methyl.

17. A compound of claim 11: 1,2′,6′-tri-N-benzyloxycarbonyl-3-azido-3-azido-3-demethoxy-4-N-methylfortimicin B.

18. A compound of claim 11: 1,2′,6′-tri-N-benzyloxycarbonyl-3-azido-3-demethoxyfortimicin B 4,5-formaldehyde oxazolidine.

19. A compound of claim 11: 1,2′,6′-tri-N-benzyloxycarbonyl-3-azido-3-demethoxyfortimicin B.

20. The compound 1,2′,6′,2″-tetra-N-benzyloxycarbonyl-3-azido-3-demethoxyfortimicin A.

* * * * *